US008992214B2

(12) United States Patent
Wu et al.

(10) Patent No.: US 8,992,214 B2
(45) Date of Patent: Mar. 31, 2015

(54) ORTHODONTIC SELF-LIGATING BRACKETS

(71) Applicant: MEM Dental Technology Co., Ltd., Tainan (TW)

(72) Inventors: Chou Bing Wu, Taipei (CN); Tsung Che Wei, Changhwu (CN); Chih Chang Tsai, Hsinchu (CN); Tung Yuo Liao, Taipei (CN)

(73) Assignee: MEM Dental Technology Co., Ltd., Tainan, Taiwan (CN)

( * ) Notice: Subject to any disclaimer, the term of this patent is extended or adjusted under 35 U.S.C. 154(b) by 0 days.

(21) Appl. No.: 13/675,709

(22) Filed: Nov. 13, 2012

(65) Prior Publication Data
US 2014/0134562 A1    May 15, 2014

(51) Int. Cl.
*A61C 7/30* (2006.01)
*A61C 7/28* (2006.01)

(52) U.S. Cl.
CPC .................................... *A61C 7/287* (2013.01)
USPC ........................................................... 433/11

(58) Field of Classification Search
CPC ............ A61C 7/12; A61C 7/14; A61C 7/143; A61C 7/16; A61C 7/28; A61C 7/287; A61C 7/30
USPC .......................................... 433/8–11, 13, 24
See application file for complete search history.

(56) References Cited

U.S. PATENT DOCUMENTS

| 5,322,435 | A | 6/1994 | Pletcher |
| 5,466,151 | A | 11/1995 | Damon |
| 6,071,118 | A | 6/2000 | Damon |
| 7,585,171 | B2 | 9/2009 | Hagelganz |
| 7,621,743 | B2 * | 11/2009 | Bathen et al. ................... 433/10 |
| 7,963,767 | B2 * | 6/2011 | Lewis et al. ..................... 433/10 |
| D648,030 | S | 11/2011 | Bryant et al. |
| 2008/0113311 | A1 | 5/2008 | Forster |
| 2010/0178629 | A1 * | 7/2010 | Oda et al. ......................... 433/14 |
| 2010/0196838 | A1 * | 8/2010 | Damon ............................ 433/10 |
| 2011/0047799 | A1 * | 3/2011 | Abels et al. ................ 29/896.11 |

OTHER PUBLICATIONS

Collinsdictionary.com. Definition of lake [retrieved on Jul. 28, 2013]. Retrieved from the Internet: http://www.collinsdictionary.com/dictionary/english/lake.*
International Search Report mailed on Feb. 27, 2014, in corresponding application No. PCT/IB2013/060064.

* cited by examiner

*Primary Examiner* — Chris L Rodriguez
*Assistant Examiner* — Justin O'Donnell
(74) *Attorney, Agent, or Firm* — Husch Blackwell LLP; Denise L. Mayfield

(57) ABSTRACT

Disclosed is a self-ligating orthodontic bracket having a mounting base with a concavely contoured surface for attachment to a tooth, a main archwire slot formed upon the base, the mounting base being supported by a bracket body, and the slot being sized for receiving an orthodontic rectangular or round archwire, a ligating slide selectively slideable between an open position permitting access to the archwire slot and a closed position covering the archwire slot. The self-ligating orthodontic bracket also includes a resilient retention feature designed for holding the ligating slide in the open or the closed positions for retreating or retaining the orthodontic archwire within an archwire slot, respectively.

17 Claims, 11 Drawing Sheets

Fig. 10B

ORTHODONTIC SELF-LIGATING BRACKETS

BACKGROUND

1. Field of the Invention

The present invention relates generally to the field of orthodontic brackets, as an improved orthodontic self-ligating bracket particularly useful in providing tooth corrective treatment to a patient is provided.

2. Related Art

Patients seeking orthodontic treatment are for the most part primarily concerned with the presence of crooked teeth, primarily in the front area of the mouth. Among the chief complaints are dental crowding, flaring, irregularity in tooth alignment, unpleasing tooth appearance, "gummy" smile, and difficulty in chewing, among other issues.

The unpleasant experiences behind these features, nonetheless, may be the result of discrepancy between the supporting bony structures that house the upper and lower dental arches. How to provide a pleasing smile and a proper chewing function while achieving a long-term detention is the ultimate goal of orthodontic treatment. Trained and experienced in skillful orthodontic technique, the Orthodontist seeks to reach these goals for the dental patient with state of the art results.

One of the primary tools employed by orthodontists is the orthodontic bracket. While many different orthodontic bracket constructs have been described, all are generally designed to achieve at least two basic objectives: to provide for attachment to a tooth, and to hold an orthodontic archwire. Both of these objectives work together to provide an orthodontic bracket that will act like an intermediate by connecting an orthodontic archwire to a tooth.

The attachment of the bracket to a tooth will transmit a force to a tooth when a resilient orthodontic archwire is bent or twisted, and then brought to engage with the bracket. This generated force can then be conveyed to the tooth. This process provides for a mechanical force system that functions to generate a force that is delivered sequentially to the teeth, thus directing teeth to the proper positions by the work of the orthodontist.

The conventional design for an orthodontic bracket permits the engagement of an archwire into an archwire slot by ligation using elastomeric or wire ligatures wrapped around the tie wings of the bracket. Ligatures or some form of fastening means are essential to secure an archwire in the bracket slot to prevent the archwire from being dislodged and thus, maintain the position of the active archwire around the dental arch. In cases where tooth extraction is deemed necessary to resolve dental crowding, the crooked teeth can be aligned and slid by orthodontic guidance along an archwire to the extracted space.

Several problems exist in the use of wire ligation for both the orthodontists and the patient. For example, because the ligature wire can trap food particles, oral hygiene care for the patient must be especially diligent throughout treatment. Also, the clinical operation to untie and retie ligature wires for each adjustment required during treatment is time consuming and tedious. Lastly, because of tooth movement that occurs along the archwire, the ligature wire binding creates resistance, resulting in a kind of friction to the tooth movement along the archwire. Thus, the intended corrective tooth movement by the orthodontic mechanical forces may be jeopardized.

To resolve these problems, passive self-ligating (or so-called frictionless) bracket systems have been developed. A separate second member, named the ligating slide, is constructed and is assembled in a self-ligating bracket system. It is displaced to open or close the archwire slot so as to retreat or retain an archwire, respectively. Meanwhile, the play between the sizes of the bracket slot and the archwire permit the sliding of the tooth along the archwire with less friction and/or resistance. In addition, because the design is without ligature wire, tooth cleansing becomes an easier chore for the patient.

In line with this notion, an immediate challenge becomes how to retain the ligating slide in the bracket while effectively maintaining the function of the slide to shift and maintain itself in the proper position. Foster and others report a construct wherein the traveling of the ligating slide can be guided and housed through the design of channels or slide slots at both sides of the brackets (Forster, US 2008/0113311A1; Bathen and Carrier, U.S. Pat. No. 7,621,743 B2; Damon, U.S. Pat. No. 6,071,118; Pletcher, U.S. Pat. No. 5,322,435; Bryant, U.S. Pat. No. D648,030 S). One bracket design uses the concept of the eccentric rotation of the ligating cover about an axial retaining pin, a third member of the bracket system (Hagelganz et al., U.S. Pat. No. 7,585,171 B2).

The designs for bracket systems are dynamic, that is they function to maintain the slide or the cover in a fixed position as open or closed. Such a design relies on a concrete locking mechanism, termed a resilient retention feature, as part of the bracket system. Generally, these resilient retention features fall into three separate groups. The first group of resilient retention features is one in which the open features appear in the outer front surface of the bracket, by including the mating devices in the outer gingival portion of the bracket body with at least one or more coplanar resilient retention features in the ligating slide (Bathen and Carrier, U.S. Pat. No. 7,621,743 B2; Hagelganz et al., U.S. Pat. No. 7,585,171 B2). The second group of resilient feature structures is one in which the hidden features have a built-in detent means, by including a raised detent projection on the recess of the bracket body and the accompanied spaced-apart circular seats on the underside of the ligating slide (Pletcher, U.S. Pat. No. 5,322,435); or by including a rib, serving as a detent, on the underside of the ligating slide with a complementary groove on the bracket body (Damon, U.S. Pat. No. 6,071,118). The third group of resilient retention features is one in which the hidden features, with a third member such as springs, and that by including a projection on the underside of the ligating slide, deflect one or two leaf springs seated in the slot-shaped recess of the bracket body (Forster, US 2008/0113311 A1); or that include a detent means in between two transverse grooves across the underside of the ligating slide, for seating a bent flat spring fitted within a recess of the bracket body (Damon, U.S. Pat. No. 5,466,151). These locking mechanisms, either with coplanar locking or with detent means in the presence or absence of the spring(s), share common physical properties provided by the ligating slides with a modified configuration.

There exist several drawbacks in these designs. For example, the open features of the locking mechanism contain the mating and the resilient retention features, that present the problem of fostering the accumulation of food debris in the areas of the locking features. Appropriate oral hygiene is difficult to maintain, and becomes a constant concern because of this lodging of food particles. Also, since the locking features with relief area built in the position overlay the archwire slot, these features may constantly encounter the increasing mechanical forces delivered by the sequential archwires, and because of this, become weaker with time. Moreover, during treatment, and when the changing of a new archwire is needed, the operator will displace the ligating slide to the (archwire slot) open position for removal of the existing archwire. Due to the improper design of securing the ligating slide in the open position, the operator may notice that the ligating slide may somehow be pushed back by the lip movement. This renders the insertion of the new archwire unfeasible. It is annoying for the operator to repeat the opening of the ligating slide. Another concern is the slipping of the ligating slide off the bracket in the self-ligating bracket system during clinic operation.

Multiple separate members in self-ligating bracket systems can be found in the group with hidden features with a detent system, and a spring which becomes a third member of the bracket. For the spring to function efficiently, it requires proper length of the spring to be seated in the slot-shaped recess of the bracket body. To accommodate this spring feature, accordingly, the labial projection of the overall bracket assembly has to be increased. This leads to an increase in the bracket thickness. Under such circumstance, a minimum thickness of the ligation slide has to be planned to house a complimentary detent and groove/recess feature in the underside. This design may assure the open and the closure of the archwire slot. However, the thickness of the bracket may disturb a patient's lip, especially when canines are in the ectopic positions. In cases where the spring feature is not considered, the resilient retention feature will have to be built in the ligating slide, the drawbacks of which were mentioned previously. Moreover, the ligation slide with its minimum thickness may gradually become strained and distorted when encountering heavier forces delivered sequentially by heavy archwires. In fact, in the clinical setting, the distorted ligation slide makes the slide opening difficult.

Self-locking or self-ligating (ligatureless) orthodontic brackets have been designed. However, most of these have complex designs, incorporating features requiring prohibitively expensive machining operations or comprising multiple separate parts, which in turn increases the number of failure modes for such brackets. Other designs have been rejected in the marketplace due to poor quality or poor design, a lack of available features, difficulty of use, or other factors.

What is needed, therefore, is an improved orthodontic bracket that incorporates a self-ligating capability and that offers a different style of bracket than those available today. Improved orthodontic brackets will also enable the orthodontic professional to more efficiently achieve the most beneficial orthodontic treatment for the patient, while at the same time reducing the various uncomfortable and unpleasant consequences to the patient noted with other types of orthodontic brackets.

The foregoing and other objectives, features, and advantages of the invention will be more readily understood upon consideration of the following detailed description of the invention taken in conjunction with the accompanying drawings.

SUMMARY OF THE INVENTION

The present invention, in a general and overall sense, provides an improved orthodontic self-ligating orthodontic bracket and a system employing the bracket in the art of orthodonture. In some embodiments, the self-ligating orthodontic bracket comprises a bracket body and a uniquely constructed ligating slide. The bracket body may be further described as comprising a mounting base having a concavely contoured surface suitable for attachment to a tooth, a main archwire slot formed upon said base, and sized for receiving an orthodontic archwire, a bracket deck and a resilient retention feature, and a ligating slide overlaying the archwire slot in a closed position. The unique resilient retention feature is constructed as part of the orthodontic bracket so as to stably and firmly hold the ligating slide in an open position for retreating the wire, or in a closed position for retaining the orthodontic wire, within the archwire slot. The bracket is also constructed in such a way as to be resistant to slippage off of the bracket body.

In some embodiments, the retention feature may be described as comprising a modified dumbbell channel that is defined by a narrow shaft and two wider spaced apart concentric circles. One of the circular ends functions as a slide stop circle, and functions to retain the ligating slide in its open position when in operation, as well as to prevent sliding movement that might result in the disengagement of the ligating slide from the bracket. The other circular end which is located adjacent to the archwire slot, presents a truncated cup-like holding circle design, and functions to secure the ligating slide in its closed position, and thereby retain the archwire within the archwire slot of the bracket. The two circular relief areas are designed to accommodate a gear, which is a cylindrical protrusion in the underside of the ligating slide, to seat in the open and the closed position.

The bracket further comprises a bracket deck. The bracket deck is characterized by several relief areas, as described below. These relief areas are suitable for the purpose of securing the open and closed position of the ligating slide of the bracket system without slipping off the bracket body.

In some embodiments, the resilient retention features reside within the bracket body of the self-ligating bracket. The resilient feature is designed to provide an S shaped resilient retention feature, that resides in between the modified dumbbell channel and the lake of the deck. The deck, in more detail, includes three elongated relief areas, namely a modified dumbbell relief area with two spaced-apart concentric circles at both ends and a detent middle portion. The lake resides in the center among the relief areas. A cylindrical post travels in between the two circles, the cylindrical post being built in the underside of the ligating slide. Thus, the concert efforts of the post in the ligating slide and relief area within the bracket body provide a controlling mechanism in the current devise construct.

The front outer surface of the device construct is smoothly designed, and is constructed so as to avoid the inclusion of unnecessary features. This plain smooth surface provides, among other advantages, the feature of not trapping any food debris or accumulation of plaque.

The ligation slide may be made of any variety of appropriate materials with strength and structural integrity, including but not limited to stainless steel or zirconia, and may be fabricated to include any variety of colors of the patients choice, so as to even further enhance patient preference and satisfaction. By way of example, the ligation slide can be made of materials such as stainless steel, ceramic, alumina or zirconia with various colors including white, black, pink, yellow, green, dark blue and others. The color coded ligating slide, by way of further example, may be fabricated so as to include the color of choice according to the patient's selection.

In some embodiments, the ligation slide may be described as having a relatively thick construction and as having sufficient structural mechanical strength strong enough to resist significant strain and/or distortion, such as that which may be caused by a heavy size archwire. The ligation slide thus is constructed so as to be capable of holding a twisted wire in a contortion that maintains a proper torque correction of the crown or root when in place in the oral cavity. In use, the ligation slide by virtue of its unique design functions to relay mechanical force to the tooth during treatment when used in concert with archwire when in use.

In some embodiments, the orthodontic self-ligating bracket may further include an auxiliary archwire slot for an additional archwire, this additional archwire being incorporated in the rotational and/or torque control of specific teeth.

Yet another feature of the orthodontic self-ligating bracket is a rugged bottom to the bracket base. This feature, among other things, functions to increase surface area for the extra-bonding materials to adhere and to produce a mechanical anchor effect to the teeth, in addition to the inherent chemical binding ability of the bonding materials.

Another aspect of the present invention provides for an improved orthodontic bracket that may be used to provide a treatment objective for the correction of rotated teeth in a patient, in particular, rotation of the front teeth. Among the crowded or crooked teeth, the main contributing factor can be defined as the rotation of a tooth or teeth. Thus, a method for the correction of a rotated tooth or teeth with the herein described orthodontic bracket system is provided, and is particularly applicable for correction of this orthodontic problem in the front area, correcting for an awkward tooth crowding situation.

The present self-ligating brackets provide for the early correction of rotated teeth with adequate time for the subsequent remodeling of the underlying tissue throughout the treatment. A wider mesio-distal dimension of the bracket width serves the purpose, for example, of rotating a tooth, among other purposes. Accordingly, the bracket widths corresponding to the mesio-distal dimension of the upper or lower teeth would appear wider or narrower within the minimal operative width, respectively. The occluso-gingival vertical heights of the brackets maintain even. In general, and in some embodiments, the front view of a bracket width reflects the width of a tooth.

The orthodontic straight wire mechanics demand that the archwire, when engaged in the archwire slot of a bracket, does not require additional bending at certain stage during, along and thereafter treatment. Thus, built-in angulations of the brackets are deemed necessary to comply with the variations in the in-and-out offset differences in the occlusal view of the dentition, in the highest contour points of the labial or buccal teeth, and in the occluso-gingival curvatures of the teeth profile relative to the related bone ridge, so called first (in and out), second (tip or tilt), and third order (torque) variations, respectively. Accordingly, the archwire slots in the current orthodontic devise are constructed to adopt these variations so as to engage a plain curved archwire at an early stage of the dental arch leveling. The bracket base with its body housing the archwire slot is built with a design of the torque-in-base by a one-piece mental injection mold (MIM). In some embodiments, the device can be formed by other materials and/or through alternative mold process, for example, by a one-piece ceramic-injection mold (CIM).

In some embodiments, the self-ligating bracket also includes a hook 15 (FIG. 11). The hook is built and added to the brackets in the distal tie wing of the gingival extension of the bracket to assist in the engagement of the power chain, coil spring or other structure(s) of the dental corrective devise. The hook may be provided as a gingival hook or a canine hook. As a gingival hook, and in one embodiment, the hook is straight in the premolar brackets. In other embodiments, the self-ligating bracket comprises a canine hook that has the configuration of an inverted L configuration with a bend toward mesial side of the tie wing of the bracket.

The foregoing and other objectives, features, and advantages of the invention will be more readily understood upon consideration of the following detailed description of the invention taken in conjunction with the accompanying drawings.

BRIEF DESCRIPTIONS OF THE DRAWINGS

For a more complete understanding of the present invention, the drawings herein illustrate examples of the invention. The drawings, however, do not limit the scope of the invention. Similar references in the drawings indicate similar elements. For consistency, whenever needed in the following figures containing two panels such as a panel A and a panel B, the same numbers referring to identical parts of the device shown in each panel were labeled.

DETAILED DESCRIPTION OF THE PREFERRED EMBODIMENTS

In the following detailed description, numerous specific details are set forth in order to provide a thorough understanding of the present invention. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Various operations will be described as multiple discrete steps performed in turn in a manner that is helpful for understanding the present invention. However, the order of description should not be construed as to imply that these operations are necessarily performed in the order they are presented, nor even order dependent.

Figure 1:
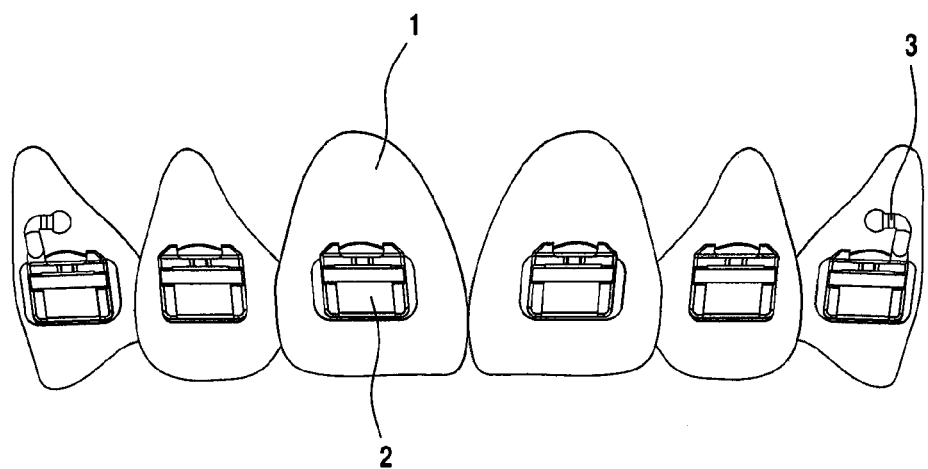
FIG. 1 is a view of self-ligating brackets in the upper front teeth.

Turning now to the several drawings, FIG. 1 depicts a frontal view of the self-ligating bracket as positioned on a typical upper tooth (1) of a patient. In this figure, the self-ligating bracket (2) is shown mounted to a tooth surface (1). A hook (3) is also shown.

Figure 2:
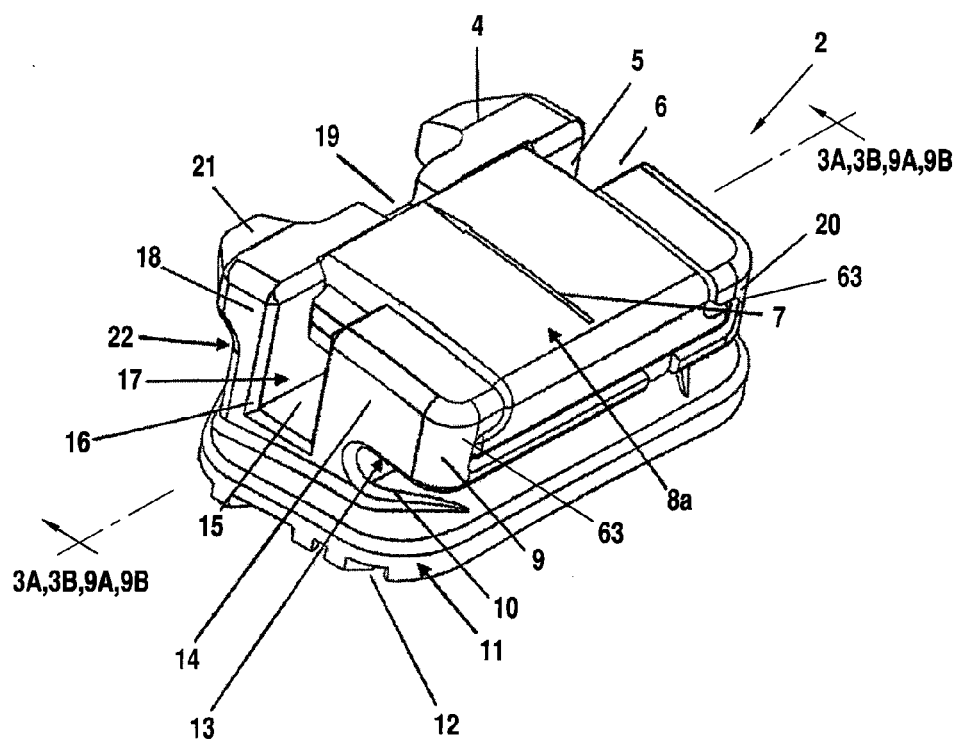
FIG. 2 is a perspective view of components of the self-ligating bracket.

FIG. 2 illustrates an exemplary isometric view of the self-ligating bracket 2 according to one embodiment of the invention. The self-ligating orthodontic bracket 2 includes a bracket base 11 for attachment to a tooth surface, and a supportive bracket body 22 for building a transverse archwire slot base 15. The archwire slot 17 is sized to receive an orthodontic archwire (not shown), and includes a bevel 16 at the edge of the archwire slot 17. The archwire slot runs parallel to the occlusal plane (a imaginary plane constructed by connecting the edges of the front teeth and the cuspids of the posterior teeth) and may be angularly oriented across the bracket when desired. The bracket base 11 has a concavely contoured surface, and includes an indented bottom 12 to enhance its attachment to a tooth. The bracket body 22 contains a gingival extension 18 and an occlusal extension 14. Both extensions of the bracket body, in concerted efforts, provide two functional domains. These functional domains are the positions of the bracket at which the tie wings which are located, with a tie wing being located at each of the four corners of a bracket (gingival tie wings, 4 and 21; occlusal tie wings, 9 and 20). The bracket also includes a transversely oriented gingival wall 5 and occlusal wall 6 for an archwire slot 17. Accordingly, a transverse archwire slot 17 is partly surrounded by a gingival wall 5, an occlusal wall 6, and an archwire slot base 15. However, a forth wall to surround the archwire slot 17 is contributed from the ligating slide 8*a*, a separate member of the self-ligating bracket, which plays an important role in opening and closing of the archwire slot 17. The archwire slot 17 is constructed so as to accommodate a rounded or a rectangular orthodontic archwire of a well-defined size, contributing to the versatility of use for clinic treatment purpose. Spaced and located in between the gingival tie wings 4 and 21 at either end is the gingival indentation 19. It is specifically designed for an Orthodontist to use a tool such as a scaler to press the ligating slide along an axial inclination of a clinical crown, and thus to open the archwire slot 17. Closure of the archwire slot 17 can be achieved by pressing in reverse direction at the bottom edge of the ligating slide 8*a*. In some embodiments, the self-ligating bracket may further include an auxiliary archwire slot 13, which is positioned so as to be received and/or threaded through a ramp 10 structure. A center line 7 is provided for visual aid in the placement of the device.

To improve patient comfort for wearing the orthodontic appliance with a mounting bracket base adhered to the tooth surface and a protrusive body, the bracket of the present invention, in some embodiments, is rounded 63 at the peripheral edges with a mild convex profile contoured to fit the patient lips. The gingival tie wings, 4, 21 at the gingival extension portion 18 are angled toward teeth surfaces, such as is depicted as a slope tapering at the junction between the gingival tie wing and the gingival extension 18. As needed in the canine and premolars, the hooks are built into the brackets for additional auxiliary usage.

The ligating slide 8*a*, inserting into the bracket body 22, in some embodiments will exhibit a smooth convex outer surface coplanar with the outer surface of the bracket body 22. The smooth polishing surface of the ligating slide is designed for ease in maintaining good oral hygiene and thus, provides a structure that deters bacterial adherence and/or plaque accumulation within the bracket, permits easier cleansing of the teeth, and particularly, reduces an "iatrogenic effect" of tooth caries and/or decalcification. Marked temporarily along the ligating slide is a center line 7 which is used to assist the orthodontists, during bracket bonding procedure, to align the bracket with the axial inclination of a clinical crown tooth. The marked center line can be easily washed or rinsed away.

Figure 3A:
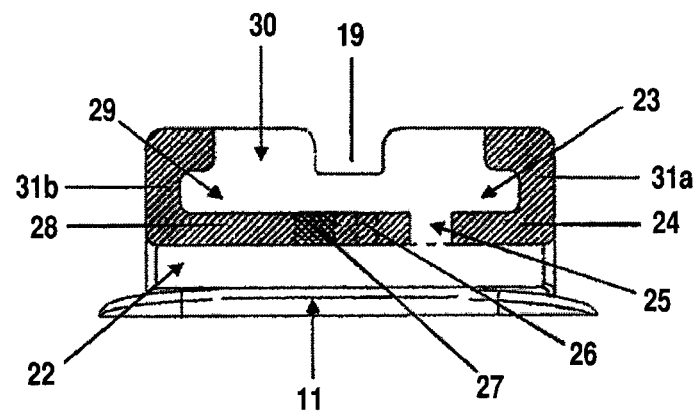
FIG. 3A is a bottom view of the occlusal extension of the bracket without a ligating slide.
Figure 3B:
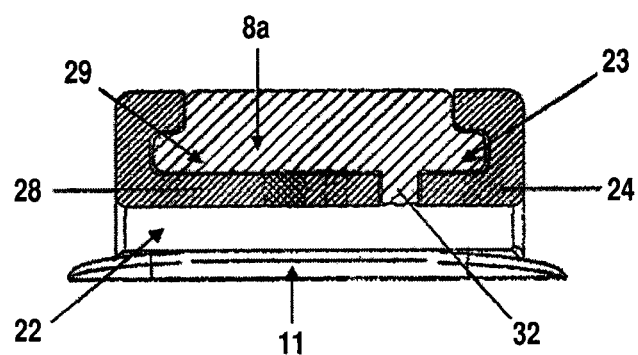
FIG. 3B is a bottom view of the occlusal extension of the bracket with a ligating slide.

Next, FIG. 3A and FIG. 3B provides a sectional view-depicted as viewed from the bottom of the occlusal extension of the bracket body 22 without a ligating slide (FIG. 3A), as well as the occlusal extension with a ligating slide 8*a* (FIG. 3B). A sectional outline of a ligating slide recess 30 depicts a rectangular yet open front form. The recess 30 is positioned in the central front part of the occlusal extension, supported by a wide flat L deck 29, and sided by two opposed inwardly projecting side walls 31*a*, 31*b*. Thus, a ligating slide recess 30 exhibits a wide open front end with two inwardly facing slide slots 23, 29 holding and enabling the ligating slide 8*a* to travel transversely from or to the archwire slot along the slide slot 23, 29. A guiding path 25 separates a wide flat deck into a major L deck 28 and a minor C deck 23. By looking at the configurations of each deck with its contiguous outer surface side walls, the major L deck 28 is arranged in a letter L configuration with a wider flat extension and a minor C deck 23, in a mirror-image letter C configuration. Separating and spacing in between the major L deck 28 and mirror-image minor C deck 23 is the guiding path 25 that directs the bar rail 32 of the ligating slide 8*a* the right path throughout. Moreover, the inward projecting side walls 31*a*, 31*b* of both L deck 29 and mirror-image C deck 23 configurations form paired, paralleled, inwardly facing slide slots (for convenience, named L slide slot 29 and mirror-image C slide slot 23) for securing and shifting a ligating slide 8*a* in proper position.

Figure 4:
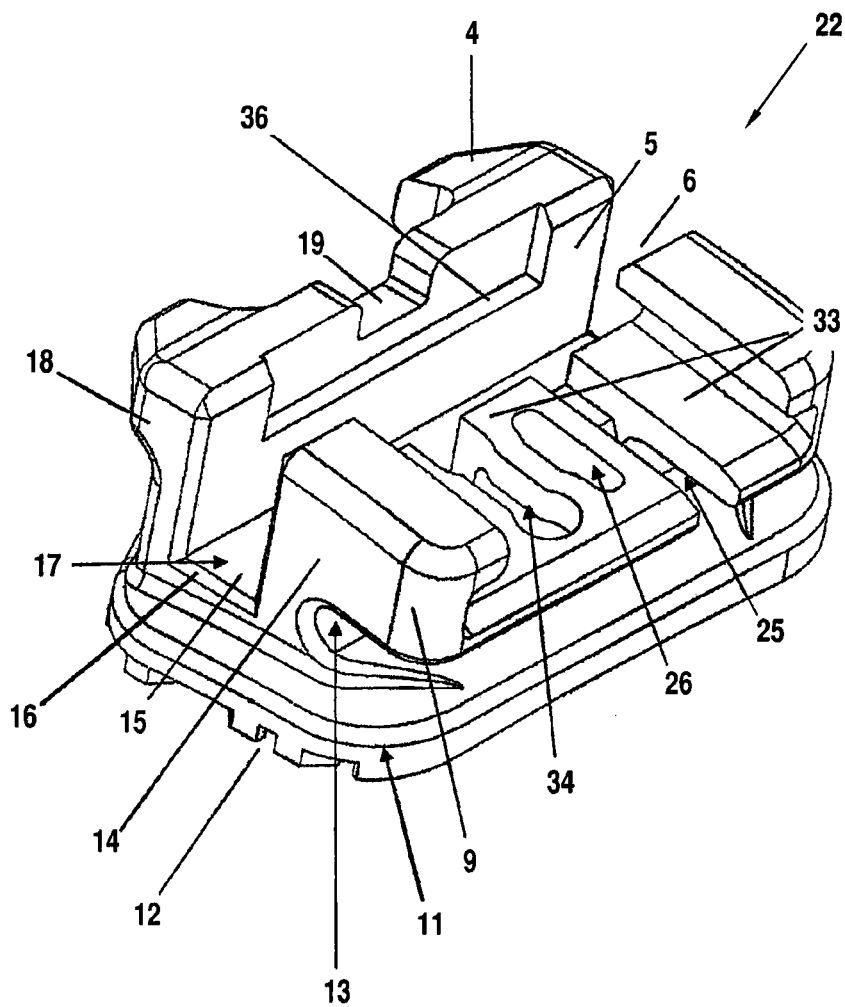
FIG. 4 is an isometric view of the bracket body.

FIG. 4 presents an isometric view of the bracket body 22 according to one embodiment of the invention. To accommodate and to seat a ligating slide (not shown), two ligating slide recesses are constructed at the gingival extension 18 and occlusal extension 14. The gingival recess is actually formed by a gingival floor 36; whereas an occlusal recess is supported by an occlusal deck 33 which plays a major role in the resilient retention mechanism for a self-ligating bracket 2 to keep the ligating slide 8*a* in the desired positions. The bracket body 22 includes several structural features, including an archwire slot 17, having an archwire slot base 15, a gingival wall 5 and an occlusal wall 6; a bracket base (mounting base) 11 having an indented bottom 35; and an auxiliary archwire slot 13. The occlusal deck 33 also includes the structural features as shown of a lake 26, a modified dumbbell channel 34; and a guiding path 25. The bracket body also provides for a occlusal tie wing 9 and a gingival tie wing 4.

The bracket 22 preferably includes rounded edges, chamfered archwire or beveled archwire slot ends 16, and an overall convex shape to improve comfort for the patient wearing the orthodontic appliance. The bracket body 22 is like an intermediate adaptor connecting an orthodontic archwire to its attached tooth. In so doing, the mechanical force generated by an orthodontic archwire can be delivered to the tooth for subsequent tooth alignment. Thus, the bracket body 22 provides at least four functions. It accommodates archwire by forming archwire slot 17 surrounded by the gingival wall 5, the occlusal wall 6, and the archwire slot base 15. It supports the ligating slide by forming a platform consisting of the occlusal deck 33 and the gingival floor 36. Moreover, it stabilizes the secures the ligating slide in the designated position by directing it through the guiding path 25 and modified dumbbell channel 34 in conjunction with the lake 26, forming a resilient retention features. Lastly, it connects bracket to the tooth surface via the indented bottom 12 of the bracket base 11. Through the use of a bonding agent, the bracket is attached to the tooth. The indented bottom 12 provides additional surface area for a bonding agent to occupy and thus to enhance the mechanical retention of the bracket body 22 to the tooth.

Figure 5A:
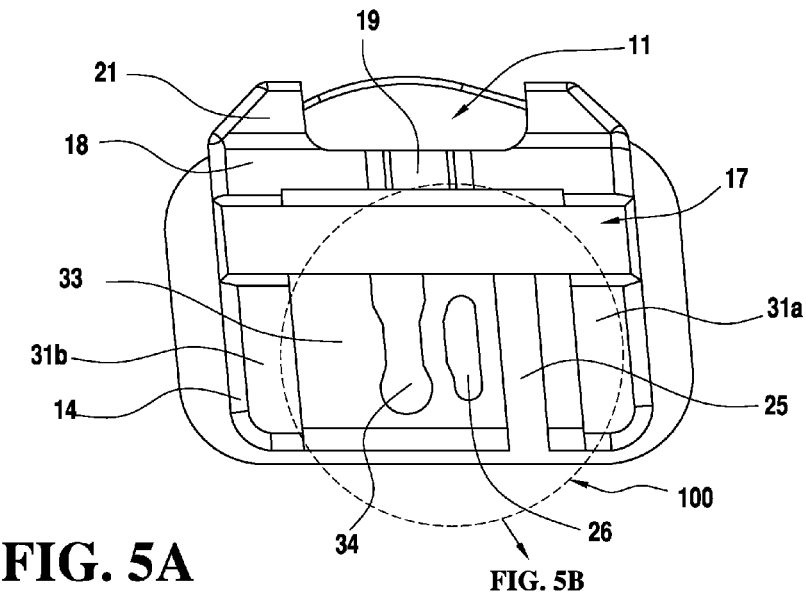
FIG. 5A is a front view of the bracket body and the resilient retention feature.

FIG. 5 depicts a front view of the bracket body and the resilient retention feature of the orthodontic bracket. In FIG. 5A, a deck 33 is provided that includes three elongated relief areas, namely, a modified dumbbell channel 34, a lake 26, and a guiding path 25, in sequence. These three relief areas align in parallel with reference to the long axis of a tooth and thus, orient themselves transverse to the archwire slot 17.

The deck 33 includes a modified dumbbell channel 34 consisting of a narrow shaft and two wider spaced-apart concentric circles 39 and 42 at both ends. This area is further described in the expanded area 100 described in greater detail in FIG. 5B). The circular end 39 remains intact, functioning as a slide stop circle to retain the ligating slide in its open position and to prevent excessive sliding movement which could disengage the ligating slide from the bracket; whereas the other circular end 42, located adjacent to the archwire slot 17, is being modified into a truncated cup-like holding circle 42 to secure the ligating slide in its closed position so as to retain an orthodontic archwire within the archwire slot 3. The two circular relief areas 39 and 42 are designed to accommodate for a gear, which is a cylindrical protrusion in the underside of the ligating slide, to seat in the open and the closed position. A gingival indentation 19 of the bracket body is also shown.

Figure 5B:
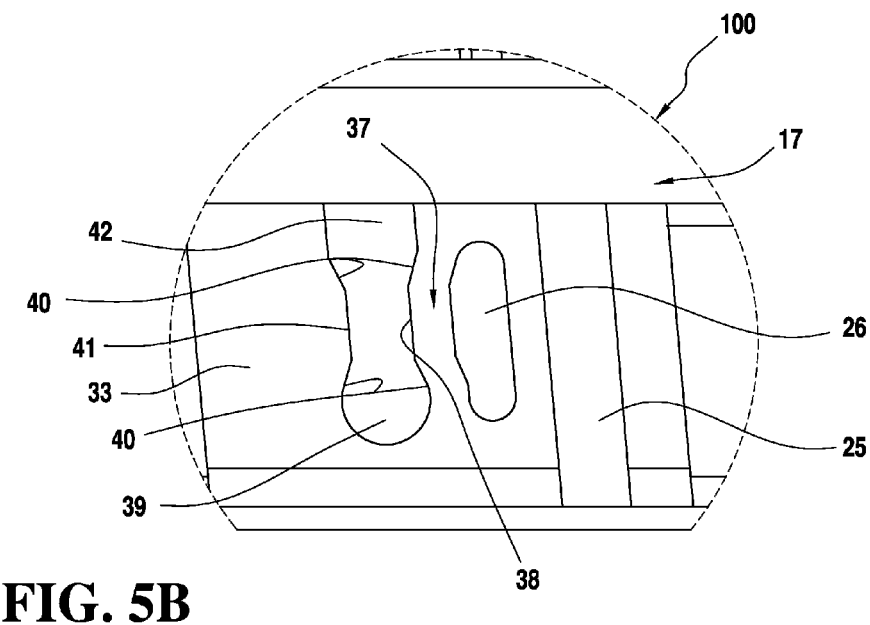
FIG. 5B is an inset with a detailed view of FIG. 5A.

FIG. 5B presents an expanded view of the bracket deck 33. A lake 26 residing in the center among the three relief areas is shown. The lake 26 permits flexing of at least portions of the resilient retention features during the shifting of a ligating slide. The resilient retention features comprise a region of the deck localizing in between a modified dumbbell channel 34 and the lake 26. This region can be regarded as a letter S configuration 37, concomitantly matching with its spring/resilient capability. Along the modified dumbbell channel 34, the S resilient retention feature 37 includes a detent 38 projection coplanar with the deck 33 and two inward curvatures 40 along the cup-like holding circle 42 and slide stop circle 39 relief area. The third component, the guiding path 25, runs through the deck, separating the deck into two parts, a minor part and a major part. It is designed to direct the bar rail of the ligating slide the right path throughout. The shaft 41 of the modified dumbbell channel 34 is also shown.

Figure 6A:
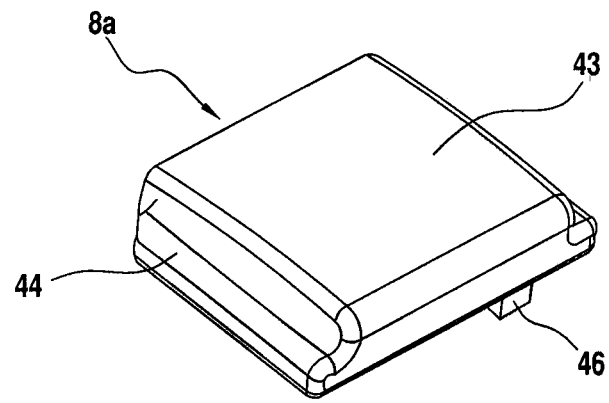
FIG. 6A is a perspective view of the outer front surface of a ligating slide.

FIGS. 6A (Outer Front Surface) and 6B (Inner Underside Surface) depicts an isometric view of the ligating slide 8a. The ligating slide 8a is a separate member of the self-ligating bracket. Nevertheless, it constitutes a major part of the front surface of a fully assembled bracket, and contains an outer front 43 and an inner underside surface 45. The outer front surface 43 of the ligating slide has a plain design with a mild smooth curvature which is aligned in coplanar relation to that of the adjacent ligature tie wings of the self-ligating bracket. The plain outer front surface 43 is esthetically pleasing and is designed to avoid any food trap or bacterial accumulation, to ease cleansing after meal, and to reduce any pathological condition such as gum swelling or tooth caries or decalcification. In so designed, a better oral hygiene can be kept throughout the treatment. Tooth brushing after each meal is regarded mandatory to avoid unwanted complication with braces. With the plain surface feature of the current ligating slide, it was found that improved oral hygiene was maintained in patients compared to patients having a self-ligating bracket of a variety of surface features, as well as compared to patients having a standard twin bracket with ligature wire tie-in orthodontic bracket. Tension in an orthodontic patient is created from constant reminders of tooth brushing in such circumstances. With the plain surface design of the present orthodontic bracket, such tension is reduced because of elimination and/or reduction to comply with rigorous tooth-brushing regimens.

Turning now to FIG. 6A, the outer front surface 43 of the ligating slide is presented. At the edges of the ligating slide are the lengthwise extension arms 44 used to travel along the slide slot of the bracket. They secure the ligating slide in its traveling positions. By resting against the side walls of the slide slots of the bracket body, the extension arm 44 also provides resistance in the torquing force generated by an intentionally twisted archwire whenever required in clinical setting. Additional guidance in the traveling of the ligating slide is reinforced by the bar rail 46.

Figure 6B:
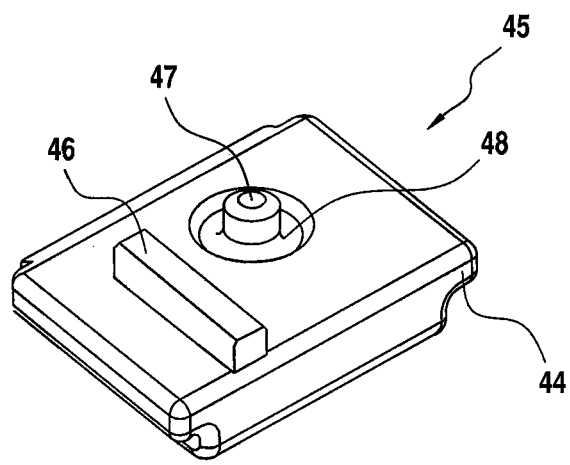
FIG. 6B is a perspective view of the inner underside surface of the ligating slide.

Turning now to FIG. 6B, the inner underside surface 45 of the ligating slide comprises two key protrusions: a bar rail 46 and a gear 47. First, a bar rail 46 is a rectangular prism oriented in transverse to an archwire slot of the bracket. The bar rail 46 is short of its main ligating slide in length on the front end, the site of which approaches the archwire slot of the bracket. In a closed position of the ligating slide, the front end of the bar rail 46 runs even with that of the adjacent occlusal decks. Thus, it seals the gap between the L and the mirror-image C decks and consolidates the occlusal wall of the archwire slot to house an orthodontic archwire. In addition, the bar rail 46 serves as a director for the ligating slide to travel through the guiding path in the deck of the bracket body. To put together, the synergistic efforts of the extension arms 44 and bar rail in the ligating slide, and the slide slots and a guiding path in the bracket body assure the straight forward movement of the ligating slide without wobbling.

The gear 47 of the ligating slide underside surface is a cylindrical protrusion that may be shifted between the stop circle and the cup-holding circle in the bracket body. The gear 47 is like a cylindrical post seating on a sunken basin below the level of the underside surface. This design to lower the position of the junction between the post and the basin is to avoid the unnecessary bumping of the junctional area into the deck of the bracket during shifting of the ligating slide. Moreover, to reduce the stress bearing generated at the junction during shifting of the gear 47, a chamfer 48 finishing is structured. Thus, with time, the gear 47 will sustain its intact structure during shifting in the open and the closed position of the ligating slide.

Figure 7A:
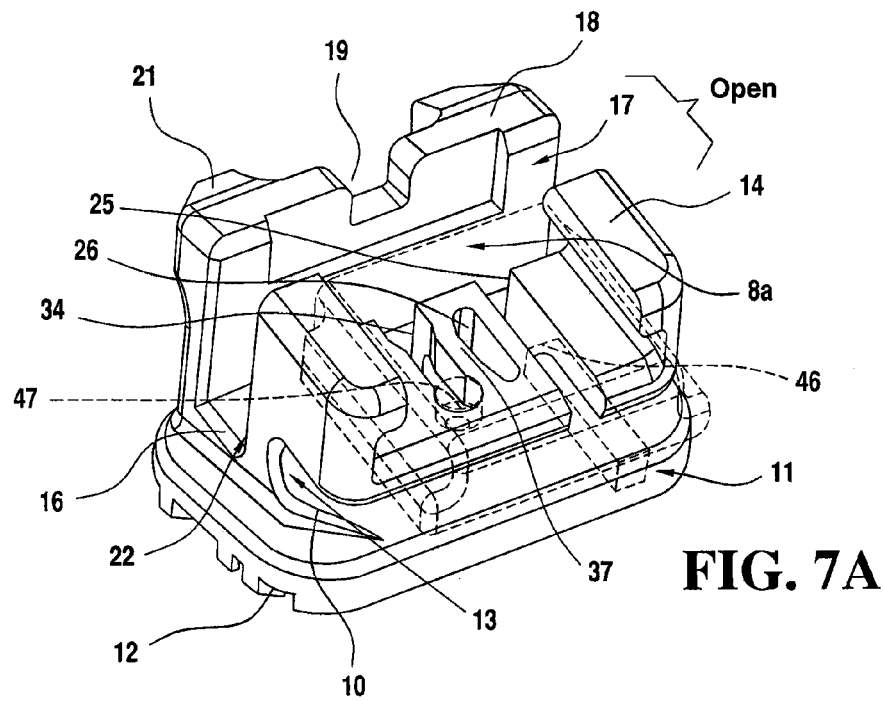
FIG. 7A is a perspective view of the self-ligating bracket in the absence of an archwire.
Figure 7B:
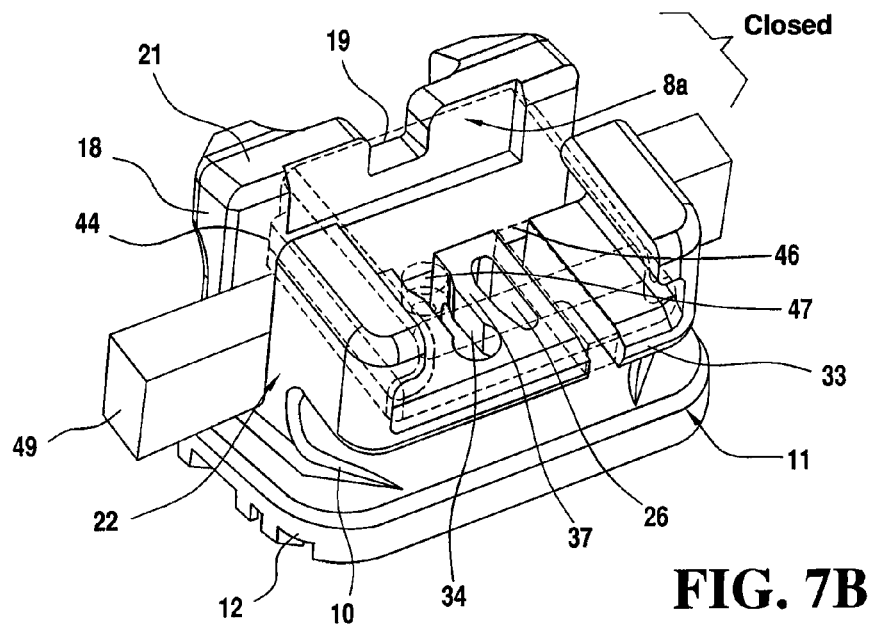
FIG. 7B is a perspective view of the self-ligating bracket in the presence of an archwire.

FIG. 7 depicts a perspective view of the self-ligating bracket in the absence (7A) and in the presence (FIG. 7B) of an archwire 49. The figure also provides a depiction of the mechanics of the opening (FIG. 7A) and the closing (FIG. 7B) of the archwire slot 17. The main function of a self-ligating bracket is to engage an orthodontic archwire 49 in the archwire slot 17 with a ligating slide 8a to replace a conventional ligature wire tie-in. Thus, the mechanics to secure and displace the ligating slide 8a in between the open and the closed position in the bracket plays an important role in keeping the archwire in place. As shown in FIGS. 7A and 7B, for the illustration of the opening and the closing of the archwire slot 17 by the ligating slide 8a, the bracket body is depicted by solid lines whereas the ligating slide is outlined by dash lines.

The bracket apparatus includes a structure that is equipped with the following elements to provide the function described herein: (1) the ligating slide 8a which occupies the recess area of the gingival extension 18 and occlusal extension 14 by seating on the respective gingival floor, and the deck is maintained by the L and the mirror-image C slide slots, (2) a solid traffic system including paired slide slots, a guiding path 25, and a modified dumbbell channel 34, (3) the resilient retention feature 37 with a S configuration, residing in between the modified dumbbell channel 34 and a lake 26. Accordingly, the detent projection coplanar with the occlusal deck 33 is the shaft of the modified dumbbell channel 34, handling the heavy traffic zone between the stop and the cup-like circles. Juxtaposed to the shaft zone of the S features are the inward curvatures of the circles.

Since the gear 47 is a solid post on a sunken basin, it glides along the inward curvature of the stop circle, for instance, and squeezes its way through the traffic zone by deflecting the shaft of the S features to the lake 26 in coplanar and transverse relation to the direction of travel of the ligating slide 8a. Meanwhile, the bar rail 46, synchronized with the gear 47 during traveling, will consolidate the guiding path 25 with its solid portion of the bar column. The consolidation will strengthen the side of the lake 26 opposite the shaft of the S feature from being displaced to the guiding path 25. In so doing, the resilient capability of the S feature is preserved. Once the gear 47 has glided to the other side of the cup-like holding circle, the shaft of the S features returns to its normal position by reflecting/spring back. Then and there, the gear 47 is retained by the inner curvature of the destined circle of the modified dumbbell channel 34. Thus, the retentive function is resumed. Simultaneously, at this juncture, the bar rail 46 mechanically seals the guiding path 25 and also, becomes a part of the occlusal wall of the archwire slot 17. The ligating slide 8a carried by the gear 47 and the bar rail 46 is now being delivered to and abuts against the gingival wall of the gingival recess, and consequently, covers the archwire slot 17. Then, the archwire 49, retained in the archwire slot 17, can implement its main function as a resilient or a stabilizing archwire, an active or a passive archwire, or a combination. Other elements of the self-ligating bracket depicted in the FIGS. 7A and 7B include: gingival extension 18, occlusal extension 14, bracket base 11, auxiliary archwire slot 13, ramp 10, indented bottom 12, bracket body 22, bevel 16, ligature tie wing 21, occlusal deck 33, extension arm 44.

Figure 8:
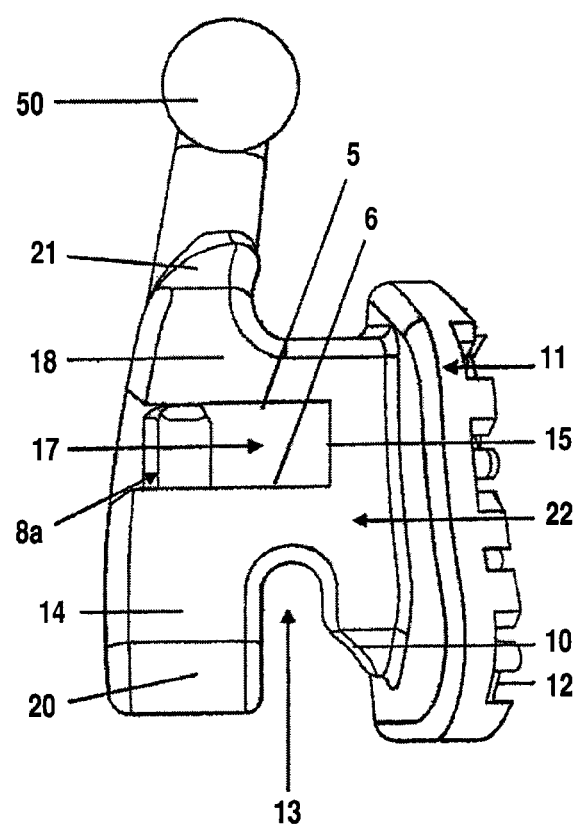
FIG. 8 is a side view of the self-ligating bracket with a hook and an auxiliary archwire slot.

FIG. 8 depicts a side view of the self-ligating bracket with a gingival hook 50 and an auxiliary archwire slot 13, as is presented in the attached figure. Besides the main archwire slot 17, an auxiliary archwire slot 13 (R archwire slot) may be built by utilizing the existing space between the deck and the base 11 of the bracket. Viewed from the side wall of the upright bracket, the configuration of the auxiliary archwire slot 13 reveals as an artistic R shape figure, for convenience, named an R archwire slot 13. The R archwire slot 13, aligned in parallel with the main archwire slot, is designed to accommodate a rectangular or round archwire with a size of up to 0.016×0.016 or 0.016 inches in diameter, respectively. For proper usage and instruction, an R slot is named. At both sides, the R ramps 10 tapering down toward the bracket base are formed to ease the insertion of the archwire. Once again, the orthodontic archwire can be retained in the closed chamber of the archwire slot 17 formed by the gingival wall 5 of a gingival extension 18, base 11, archwire slot base 15, the occlusal wall 6 of an occlusal extension, and the inner slide of ligating slide 8. Also depicted in FIG. 8 are: a bracket body 22, a ramp 10, an indented bottom 12, an occlusal ligature tie wing 20, and a gingival ligature tie wing 21.

The inclusion of a second archwire in conjunction with a main archwire (so called twin wire technique or mechanics) creates two point contacts in the bracket. By synchronizing the delivered orthodontic forces, twin wires facilitate the correction of the rotated and uprighted teeth (i.e., first and third order correction).

In another embodiment, and as shown in FIG. 8, a rectangular archwire may be used in the main slot 17 and a second archwire may be used in the R slot 13, and in so doing will enhance the torque (third order) correction of the teeth. Take an example of a case presented with an Angle Class II division 2 malocclusion where the anterior upper teeth are too uprighted. Because the upper lip goes along the root and the crown of the front teeth, too uprighted front teeth may lead to an obtuse nasolabial angle, an unpleasing lip appearance. Hence, depressing down the roots lingually (i.e., lingual root torque) becomes necessary to provide a curved upper lip with a mild protrusive cupid appearance. To achieve this, an active delivery force shall be created by twisting the front teeth segment of the main archwire. This is the mechanism by which lingual root torque is added to correct the overly uprighted upper front teeth to a normal tooth position. The concept can be explained by the illustration (FIG. 8) of the side view of the self-ligating bracket. The mechanical force generated by the twisted main archwire is transmitted to the tooth via bracket. Then, the force-inducted bracket pivoting will be centered around the main archwire slot 17. Meanwhile, the gingival hook 50 (oriented toward the gum and the root of a tooth) and gingival extension 18 will be spinning toward bracket base 11; whereas the occlusal extension 14 will be spinning away from the bracket base 11, which is considered as a side effect in uprighting a tooth. By seating a passive second archwire in the auxiliary archwire slot 13, it can stop the side spinning effect. Accordingly, the twisted archwire can deliver its active mechanical force to do the work on lingual root torque.

The following is how clinic works. When inserted into the archwire slot 17 of a bracket, the passive buccal/posterior segment of the archwire seats in the brackets of the posterior teeth, whereas the anterior clockwise-twisted segment of the full size archwire will actively impinge on the surrounding walls of the archwire slot 17 of the brackets in the front teeth. Thus a torquing moment (clockwise rotation) will be generated and transmitted to the front teeth. However, the rotation will be centered on the main archwire. Then, a second archwire is placed in the auxiliary archwire slot 13 formed by the undersides of the occlusal extension 14 and the occlusal ligature tie wing 20, and by the portion of the lower part of the bracket body 2 adjacent of the ramp 10. It connects and binds together the entire front and posterior teeth in one dental arch as an anchorage unit. In so doing, the rotational center will be changed to and fixed in the R archwire slot 13. Thus, with a solid anchorage unit, the second archwire can be used to minimize the side effect of the twisted main archwire against the walls of the main archwire slot, and assist the main archwire in excelling the torquing energy. Moreover, the orientation of the main archwire slot 17 and the R archwire slot 13 is such that the orthodontic forces generated by the main archwire and the auxiliary archwire can be transmitted evenly through the indented bottom 12 along the bracket base 11 to the tooth. Accordingly, the bracket will not be debonded. The gingival hook 50 provides an additional connection between teeth through elastic chain during tooth movement. Even in orthognathic (jaw) surgery, the gingival hooks 50 will be used to stabilize upper and lower dental arches by ligature wire-tying through upper and its counterpart lower teeth. Concomitantly, the tooth containing, surgically sec sectioned jaws to be immobilized.

Figure 9A:
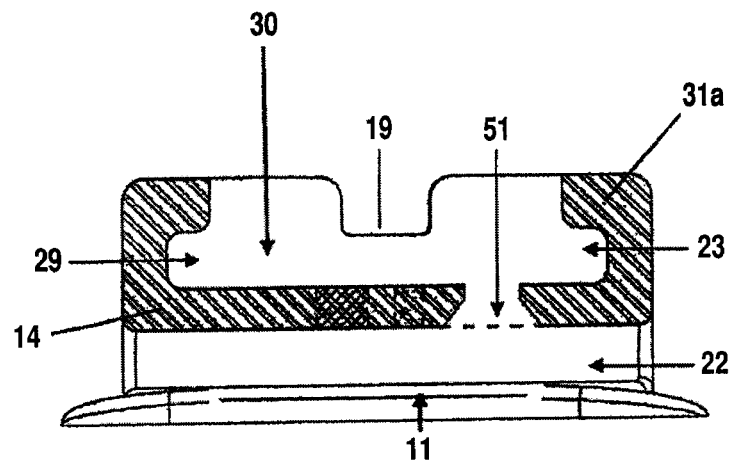
FIG. 9A is a view of a modified bar rail and guiding path without a ligating slide.
Figure 9B:
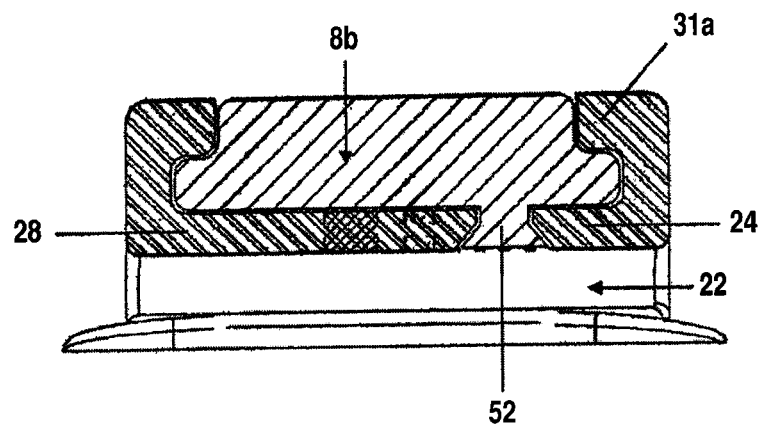
FIG. 9B is a view of a modified bar rail and guiding path with a ligating slide.

FIG. 9 provides a depiction of a modification of the bar rail and the guiding path of the orthodontic self-ligating bracket. Turning now to FIG. 9A, a modification is depicted wherein the cross section of the guiding path between the L deck 28 and mirror image C deck 24 of the occlusal deck. The formerly designed parallel lines of the walls along the guiding path 51 are now modified into a negative dove-tail shape of the guiding path 51. On the other hand, the positive or mate counterpart is constructed in the dove-tail rail 52 of the underside of the ligating slide 8b. The ligating slide 8b, while seating on the ligating slide recess 30, can be glided along the L slide slot 29, mirror image C slide slot 23, and dove-tail shape guiding path 51. In addition, the ligating slide 8b is secured and stabilized not only by the existing inward projecting slide walls 31a but by dove-tail configuration of the rail 52. In general, the dove-tail structure creates an "under cut" function to further sustain the ligating slide 8b from flipping out due to the torque effect by the strained archwire.

The device in some embodiments includes certain features with modifications of the self-ligating bracket that are designed to comply with circumstances arising from a particular tooth position in a patient. For example, in the case of an Angle Class II Div 2 malocclusion, the upper front teeth (incisors) are tooth uprighted. To obtain proper crown angulation of the uprighted teeth requires labial crown torque or lingual root torque of the teeth by twisting the needed front portion of the archwire. Under such circumstance, the mechanical loading of the ligating slide increases. By including a dove tail configuration in the bar rail 52 and the corresponding guiding path 51 (FIG. 9), the undercut area will hold the ligating slide 8b and guiding path 51 firmly in addition to the existing slide slots 23,29. In so doing the twisted archwire is securely retained in the archwire slot of the bracket. Meanwhile, the ligating slide will not be peeled off the bracket. Thus, the mechanical force can be transmitted through the bracket to the teeth to be corrected.

Figure 10A:
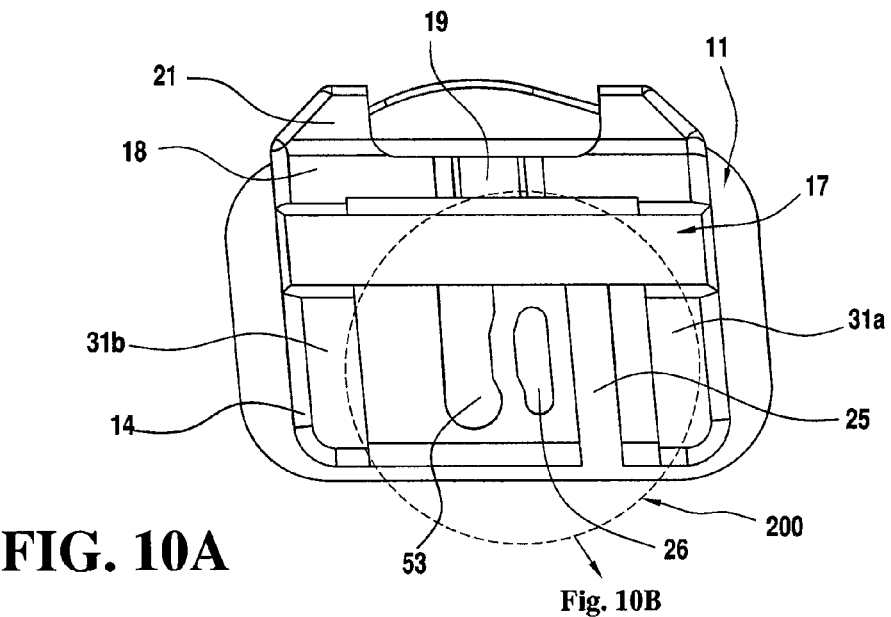
FIG. 10A is a top view of a reconfiguration of the modified dumbbell channel.
Figure 10B:
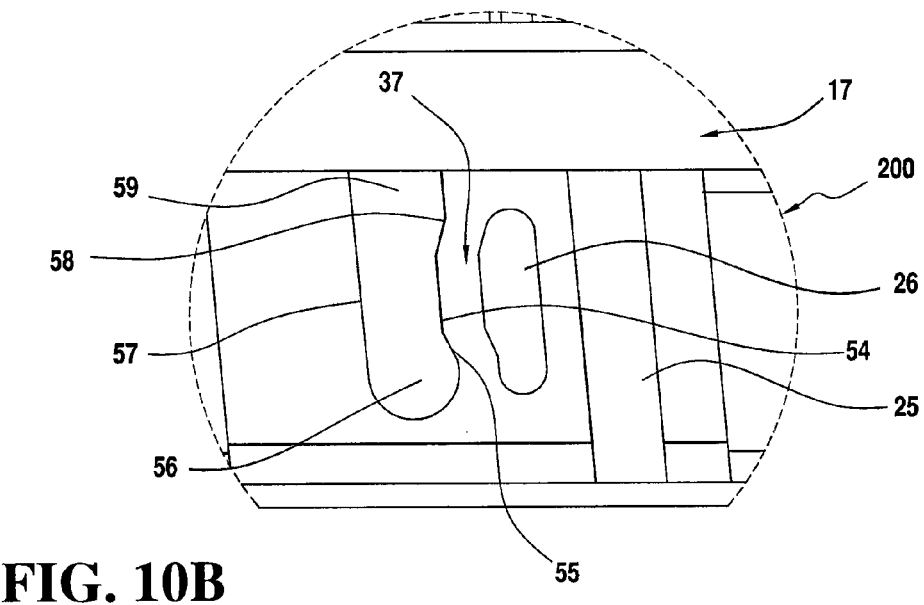
FIG. 10B is an inset with a detailed view of FIG. 10A.

The preferential locking mechanism can also be obtained by the changes in the modified dumbbell channel (FIG. 10). FIG. 10 presents a reconfiguration of the modified dumbbell channel 53. The modified dumbbell channel 53 (FIG. 10A) is used for the ligating slide to shift from the slide stop circle 56 (see detail 200 in FIG. 10B) in an archwire slot 17 open position to the cup-like holding circle 22 in an archwire slot 17 closed position. The resilient retention S feature 37 adds the flexibility to the shifting process by the design of the detent 54 and the lake 26. The shifting is firmly directed by the guiding path 25 as well as the inward projecting side walls 31a, 31b at both sides built along the occlusal extension 14 and is stopped at the front end of the gingival extension 18. The shifting begins with a gliding along the inward curvature 58 of the cup-like opening 59 or the inward curvature 55 of the slide stop circle 56 (FIG. 10B), then a passing or squeezing through the detent 54 of the resilient retention S feature 37 along the lake 26 to the other end of the circle. The device is an efficient and effective tool to shift the ligating slide so as to retreat or inset the archwire to the bracket and keep the ligating slide in position without using the ligature wire-tie procedure. Thus, the opening and closing of the ligating slide can be operated with constant force through use of an orthodontic tool, such as scaler. Nonetheless, when the brackets are placed in the lower front small teeth, incisors, it was noticed that the standard operating force to open the ligating slide could be effectively reduced to achieve the added benefit of minimizing any painful feeling to the patient. In line with this notion, the modified dumbbell channel was also configured, in some embodiments, to allow less delivery of the clinic operation force to open or close the ligating slide. While the S resilient retention features 37 with a detent 54 and inward curvatures 55,58 of the circles 56,59 (FIG. 10B) remain intact, the counterpart side of the channel is being adjusted and simplified by a straight line, named coast line 57, instead. Thus, the constraint reduces to some extent when the gear of the ligating slide shifts along the reconfigured modified dumbbell channel 53. In fact, the reconfiguration of the modified dumbbell channel can be applied to all the brackets should the reduction of the open loading dictate.

Figure 11:
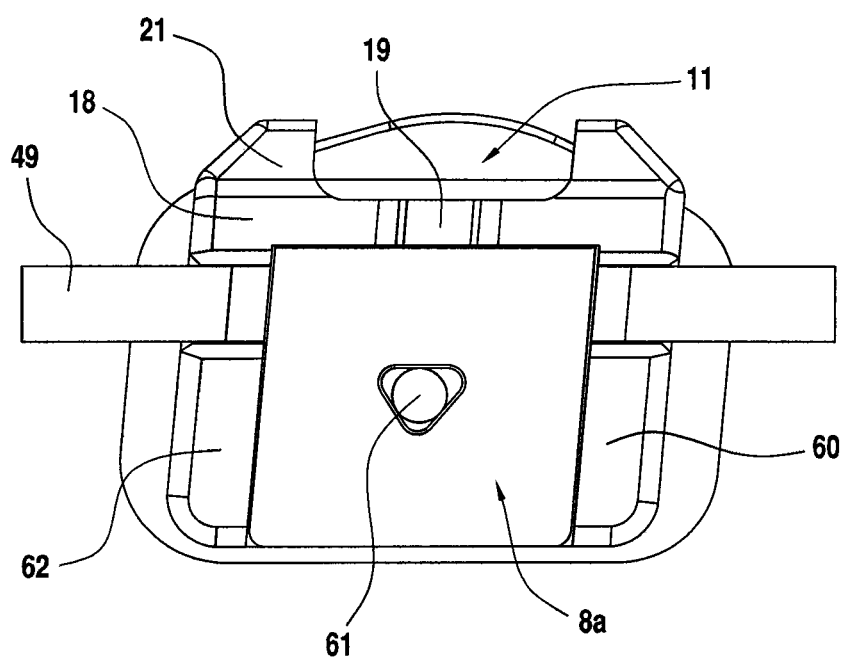
FIG. 11 is a front view of the self-ligating bracket.

FIG. 11 depicts a front view of the self-ligating bracket. The following structures are depicted in the figure: gingival indentation 19, bracket base 11, inward projecting side wall 60, ligating slide 8a, indentation 61, occlusal extension 62, archwire 49, gingival extension 18, gingival tie wing 21. The design of the gingival indentation 19 is to provide an access to open the ligating slide 8a. It resides in the middle of the gingival extension 18 with the gingival tie wing 21 at both sides. The ligating slide 8a travels along the slide slot formed by inward projecting side walls 60 in the occlusal extension 62 toward the gingival indentation 19 to close the archwire slot so as to secure an archwire 49. The opening of the ligating slide (in FIG. 11) becomes a simple press or push downward effort. However, most self-ligating brackets use a front access in the ligating slide to open or close the archwire slot by shifting the ligating slide. The steps to open the ligating slide require first press and then pull downward efforts. The operators may be used to such design. Thus, and in some embodiments, whenever required, another access maybe build, an indentation 61, in the front surface of the ligating slide 8a for the operator to open the ligating slide. Nevertheless, the rest of the front surface of the ligating slide remains plain.

The invention of the self-ligating bracket can be made of several different materials including stainless steel, nickel free titanic alloy, plastic, ceramic, or zirconia. Particularly, efforts are made for the interests of the patients to combine and to assemble a metal bracket with a zirconia ligating slide exhibiting variety of colors including white, black, pink, yellow, green, dark blue and others. The color coded ligating slide adds another option that may be used to customize the device according to the preferences and selection of the patient.

The development of the self-ligating bracket improves clinical operation and patient compliance in oral hygiene care. Central to the development of the bracket is the locking and retaining mechanism which adds to the usefulness of the bracket. A gear shifting system is provided with the present bracket that efficiently handles the traveling of the ligating slide, and the retreating and retaining of the archwire in the archwire slot.

The self-ligating bracket as described herein is hygienic, with its ligating slide easy to be displaced by pressing along the axial inclination of the crown. It provides a straight forward displacement of the ligating slide without wobbling. A clicking sound can be heard when the S resilient retention features return to its normal position the moment the gear of the ligating slide is being displaced from the detent projection of the S features to the destined circle. In the open or the closed position, the ligating slide is retained by the inward curvature of either circle. Thus, a sequential slide-click-retain motion assures the opening and the closing of the ligating slide to allow the respective retreating and the retaining of the archwire in the archwire slot.

In some embodiments, the self-ligating bracket may include an auxiliary archwire slot. This auxiliary archwire slot is provided in order to include any number of additional uses as may be desired by the attending dentist or dental professional. The ultimate goals in this invention are to ease clinical operation by equipping the Orthodontist with an efficient self-ligating bracket system, and to facilitate simpler tooth cleansing for the patients to maximize good oral hygiene care throughout orthodontic treatment.

The improved orthodontic bracket described herein may comprise any of a wide variety of materials suitable for use in an orthodontic appliance. Such materials have commonly included plastics, ceramics, stainless steel, titanium, or other metal alloys. The bracket preferably comprises a biocompatible material with corrosion resistive properties, and the bracket preferably comprises materials which may be formed into the structure shown yet maintaining suitable strength characteristics for retaining commonly used orthodontic archwires or other components of an orthodontic appliance.

Nickel may be the most common metal associated with contact dermatitis in orthodontics. Recent figures suggest that perhaps 10% of patients are sensitive to nickel. Nevertheless, nickel-containing metal alloys, such as nickel-titanium and stainless steel, are widely used in orthodontic appliances. Nickel-titanium alloys may have nickel contents above 50% and may potentially release enough nickel in the oral environment to elicit manifestations of an allergic reaction. Stainless steel has a much lower nickel content, perhaps around 8%, and, because the nickel is bound in a crystal lattice within stainless steel, the nickel may be less available to react. Consequently, stainless steel orthodontic components may be less likely to cause nickel hypersensitivity. However, because of the remaining uncertainty regarding a particular patient's sensitivity to nickel, it may be desired to provide nickel-free orthodontic brackets to avoid nickel hypersensitivity altogether. Therefore, the improved orthodontic bracket described herein preferably comprises a nickel-free material. In one embodiment, the bracket comprises a nickel-free cobalt-chromium alloy.

Several methods may be used to manufacture the improved orthodontic bracket described herein. For example, the bracket may be cast, machined, injection molded and so on. Injection molding of plastics may be used as may be ceramic injection molding (CIM) or metal injection molding technique, depending upon the materials chosen. Further, the bracket may comprise multiple assembled components. For instance, the bracket may comprise the assembly of a formed bracket body and a formed ligating slide member, the ligating slide member retained within the channel of the bracket body following a coining operation whereby the channel sides are crimped inward along the sides of the ligating slide member (forming a dovetail joint). A ball hook may be welded to the bracket assembly, and a wire mesh may be adhered to the mounting base of the bracket to improve its bonding surface.

In one embodiment, the improved orthodontic bracket base is formed of nickel-free cobalt chromium using a metal injection molding (MIM) process, whereby the ligating slide member is similarly constructed and attached using a coining operation to crimp the sides of the bracket base (bracket body). In one embodiment, the improved orthodontic bracket comprises a one-piece molded bracket body and a one-piece molded ligating slide member, the ligating slide member assembled to the bracket body using the aforementioned coining operation.

As commonly practiced in orthodontic treatment, brackets may be fabricated for a particular patient by prescription. The brackets may be engineered to include the appropriate slot torque and slot tip for each individual tooth for the particular patient. For example, specifically engineered brackets may be fabricated for the upper left central, the upper left lateral, the upper left cuspid, and so forth moving distally toward the upper left molars (using Palmer's notation for designating individual teeth). Each bracket typically incorporates a particular slot torque and slot tip as well as other features as may be needed. For instance, the bracket for the upper left cuspid may include a slot tip and torque of, perhaps, +8 and −7 degrees (in MBT prescription) or +11 and 0 degrees (in Roth prescription), respectively, and include a ball hook for use with elastics or other features of the orthodontic appliance. Such a bracket may have the features as in FIG. 2, 4, or 7.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

What is claimed is:

1. A self-ligating orthodontic bracket system having resilient retention features comprising:
    a) a bracket body having an outer surface and an inner surface, said bracket body comprising:
        a mounting base with a concavely contoured surface suitable for attachment to a tooth;
        a main archwire slot formed upon the mounting base, supported by the bracket body, and sized for receiving an orthodontic archwire;
        a deck comprising a ligating g slide recess, a modified dumbbell channel having a first curved side and a second opposing side being straight, the first side and second side being joined by a curved portion, and a lake defined by an enclosed space positioned on the first side of the modified dumbbell channel; and
        a resilient retention S feature positioned between the first side of the modified dumbbell channel and the lake;
    b) a ligating slide that is slidably received into the ligating slide recess of the deck, said ligating slide being selectively slidable between an open position so as to provide access to the archwire slot, and a closed position that provides for a covering of the archwire slot,
wherein the lake is configured to allow flexing of the resilient retention S feature during movement of the ligating slide, wherein said resilient retention S feature holds the ligating slide in an open position for retreating, or a closed position for retaining the orthodontic archwire within the archwire slot, and wherein the ligating slide is positioned with the bracket body so as to be resistant to slippage off the bracket body.

2. The self-ligating orthodontic bracket system of claim 1 wherein said deck comprises a guiding path.

3. The self-ligating orthodontic bracket system of claim 1 wherein said ligating slide comprises an outer front surface and an inner underside surface.

4. The self-ligating orthodontic bracket system of claim 3 wherein said inner underside surface comprises a cylindrical post.

5. The self-ligating orthodontic bracket system of claim 3 wherein said inner underside surface of the ligating slide comprises a bar rail.

6. The self-ligating orthodontic bracket system of claim 3 wherein said outer front surface of the ligating slide comprises an extension arm.

7. The self-ligating orthodontic bracket system of claim 1 wherein the ligating slide is comprised of stainless steel, plastic, ceramic, alumina or zirconia.

8. The self-ligating orthodontic bracket system of claim 1 further comprising an auxiliary archwire slot formed below the main archwire slot, wherein said auxiliary archwire slot is suitable for receiving a second orthodontic rectangular or round archwire.

9. The self-ligating orthodontic bracket system of claim 1 wherein the body outer surface is smooth and is absent protrusive structures.

10. The self-ligating orthodontic bracket system of claim 1 wherein the ligating slide is provided in a color white, black, pink, yellow, green or dark blue.

11. The self-ligating orthodontic bracket system of claim 1 wherein the bracket body has a bottom surface that is rugged so as to increase surface contact area for a bonding material and to produce additional mechanical anchoring to the teeth.

12. The self-ligating orthodontic bracket system of claim 1 further comprising a hook.

13. The self-ligating orthodontic bracket system of claim 12 wherein the hook is a canine gingival hook or a gingival hook.

14. The self-ligating orthodontic bracket system of claim 12 wherein the hook is a gingival hook having an inverted shape or is a straight premolar gingival hook.

15. The self-ligating orthodontic bracket system of claim 1 wherein the modified dumbbell channel includes a circle at each of a first and a second end of the channel, the circles separated by a detent, wherein the detent and the curvatures of the circles remain intact on the first curved side and become a straight line on the second opposing side of the channel.

16. The self-ligating orthodontic bracket system of claim 1 wherein the ligating slide recess of the deck further comprises a guiding path having a dove-tail configuration.

17. The self-ligating orthodontic bracket system of claim 16 further defined as comprising a configuration that permits a mate dove-tail rail in the ligating slide.

* * * * *